United States Patent [19]

Elliott et al.

[11] Patent Number: 4,923,502
[45] Date of Patent: May 8, 1990

[54] TRIAZOLYL ETHANOL DERIVATIVES AS PLANT GROWTH REGULATORS

[75] Inventors: Raymond Elliott, Lower Earley, Nr Reading; Raymond L. Sunley, Twyford, both of England

[73] Assignee: Imperial Chemical Industries PLC, London, United Kingdom

[21] Appl. No.: 10,446

[22] Filed: Feb. 3, 1987

[30] Foreign Application Priority Data

Feb. 18, 1986 [GB] United Kingdom ............... 8603951

[51] Int. Cl.$^5$ .............. C07D 249/08; A01N 43/653
[52] U.S. Cl. .............................. 71/92; 71/76; 548/267.8
[58] Field of Search .............. 548/262; 71/76, 92

[56] References Cited

U.S. PATENT DOCUMENTS

| | | | |
|---|---|---|---|
| 4,507,140 | 3/1985 | Sugovanam | 71/76 |
| 4,551,469 | 11/1985 | Parry et al. | 548/262 |
| 4,603,140 | 7/1986 | Reiser et al. | 548/262 |
| 4,723,984 | 2/1988 | Holmwood et al. | 548/262 |
| 4,747,869 | 5/1988 | Kramer et al. | 548/262 |

FOREIGN PATENT DOCUMENTS

| | | |
|---|---|---|
| 0086173 | 8/1983 | European Pat. Off. |
| 0086304 | 8/1983 | European Pat. Off. |
| 126430 | 11/1984 | European Pat. Off. |
| 2064520 | 6/1981 | United Kingdom ............... 548/262 |
| 2129000 | 5/1984 | United Kingdom ............... 548/262 |

OTHER PUBLICATIONS

Nyfeler, et al, "1-Triazolylethylether, Etc.," CA103:7139s (1985).
Chem. Abstracts, vol. 104(21) No. 186424k, Registry Nos. 101975-39-7 and 101975-42-2.

Primary Examiner—Glennon H. Hollrah
Assistant Examiner—Patricia L. Morris
Attorney, Agent, or Firm—Cushman, Darby & Cushman

[57] ABSTRACT

Triazolyl alcohol derivatives active as plant growth regulating have the general formula:

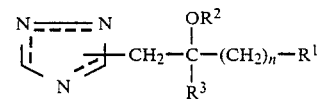

wherein $R^1$ is a cycloalkyl or cycloalkenyl group containing from 3 to 8 ring carbon atoms and optionally substituted, for example by lower alkyl or halogen; n is 0 or 1 or 3; $R^2$ is hydrogen or lower alkyl; and $R^3$ is a tertiary butyl group optionally substituted by one or more halogen atoms. Triazol-1-yl derivatives are preferred.

6 Claims, No Drawings

TRIAZOLYL ETHANOL DERIVATIVES AS PLANT GROWTH REGULATORS

This invention relates to heterocyclic compounds useful as plant growth regulating agents, to processes for preparing them, to compositions containing them and to methods of regulating plant growth using them. In particular, this invention relates to triazolyl alkanols.

According to the present invention there is provided a triazole derivative having the general formula (I):

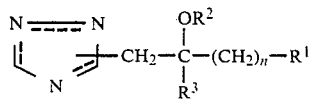

and stereoisomers thereof, wherein $R^1$ is an optionally substituted cycloalkyl or cycloalkenyl group containing from 3 to 8 carbon atoms in the cycloalkyl or cycloalkenyl ring: n is 0 or 1 or 3; $R^2$ is hydrogen or an alkyl group containing from 1 to 4 carbon atoms; and $R^3$ is a tertiary butyl group optionally substituted by one or more halogen atoms.

The compounds of the invention contain at least one chiral centre. Such compounds are generally obtained in the form of racemic mixtures. However, these and other mixtures can be separated into the individual isomers by methods known in the art, and this invention embraces such isomers.

Formula (I) embraces compounds in which the triazole ring is substituted in the 1- (asymmetrical) position or in the 4- (symmetrical) position to form the triazolyl derivative of the present invention, and the present invention includes such compounds both separately and in admixture. The triazole ring is preferably substituted in the 1-position to give a triazol-1-yl derivative. However, since certain preparative methods may produce a mixture of 1- and 4-substitution, such a mixture may be used if desired without further separation of the components.

Preferred groups $R^2$ are hydrogen or methyl.

The cycloalkyl or cycloalkenyl group $R^1$ may be substituted for example by one or more lower alkyl groups (for example alkyl groups containing from 1 to 4 carbon atoms, for example one or more of methyl, ethyl, propyl (n or iso) or one or more halogen atoms. As examples of the group $R^1$ there may be mentioned optionally substituted cyclopropyl, cyclobutyl, cyclopentyl, cyclohexyl, cyclopentenyl and cyclohexenyl.

$R^3$ may be the tertiary butyl group, that is the group:

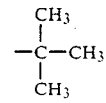

The tertiary butyl group may be optionally substituted by one or more halogen atoms, for example one or more fluorine atoms to give groups such as:

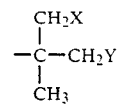

wherein X is Cl or F and Y is Cl, F or H.

n Is preferably 0 or 1.

The present invention includes salts, esters and metal complexes of the compounds of formula (I) wherein $R^2$ is hydrogen. As examples of esters there may be mentioned for example acetates or benzoates. Without limitation of the generality of the above statement, the present invention also includes any compound which breaks down in agrochemical use to form a compound of formula (I).

Examples of the compounds of the invention are shown in Table I below in which the different values for $R^1$ and $R^2$ and $R^3$ in the general formula (I) above are presented.

TABLE I

| Compound No. | Position of substitution in triazole ring | $(CH_2)_n$-$R^1$ | $R^2$ | $R^3$ | Melting Point (°C.) |
|---|---|---|---|---|---|
| 1 | 1- | —CH$_2$—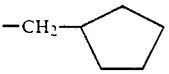 | H | *tBu | 55.5–58 |
| 2 | 4- | —CH$_2$—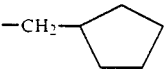 | H | *tBu | 167–169 |
| 3 | 1- |  | H | *tBu | 80.5–82.5 |
| 4 | 1- |  | H | *tBu | 94–99.5 |
| 5 | 1- | 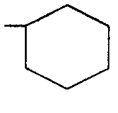 | H | *tBu | 100.5–101.5 |
| 6 | 1- | —CH$_2$— | H | *tBu | 73–75 |

TABLE I-continued

| Compound No. | Position of substitution in triazole ring | $(CH_2)_n-R^1$ | $R^2$ | $R^3$ | Melting Point (°C.) |
|---|---|---|---|---|---|
| 7 | 1- | —CH₂—cyclohexyl | H | *tBu | 81.5–83 |
| 8 | 1- | cyclopentyl | H | *tBu | 89 |
| 9 | 1- | —CH₂—(cyclopentyl-3-CH₃) | H | *tBu | 52–67 Mixture of diastereo-isomers |
| 10 | 1- | —CH₂—(cyclopentyl-2-CH₃) | H | *tBu | Oil Mixture of diastereo-isomers |
| 11 | 1- | (cyclopropyl)—CH₃ | H | *tBu | 95–101 8:1 Mixture of diastereo-isomers |
| 12 | 1- | —CH₂—cyclopentenyl | H | *tBu | 86–89 Mixture of diastereo-isomers |
| 13 | 1- | —CH₂—cyclopropyl | H | *tBu | 77–79.5 |
| 14 | 1- | —CH₂—(cyclopentyl-3-C₂H₅) | H | *tBu | Oil Mixture of diastereo-isomers |
| 15 | 1- | —CH₂—(cyclopentyl-2-C₂H₅) | H | *tBu | Oil Mixture of diastereo-isomers |
| 16 | 1- | —CH₂—(cyclopentyl-2,4-(CH₃)₂) | H | *tBu | Oil Mixture of diastereo-isomers |

*tBu represents the tertiary butyl group

The compounds of general formula (I) wherein $R^2$ is hydrogen may be prepared by reacting a compound of general formula (II a) or (II b).

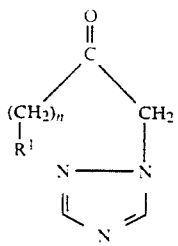

(IIa)

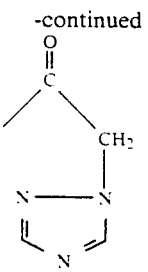

(IIb)

wherein $R^1$ and $R^3$ are defined above, with an organometalic compound which may be represented by the general formula (III b) or (III a) respectively.

$$R^1(CH_2)_nM \quad \text{(IIIa)}$$
$$R^3M \quad \text{(IIIb)}$$

wherein $R^1$ and $R^3$ are as defined above and M is a suitable metal which is preferably lithium, magnesium, titanium or zirconium. The reaction conveniently takes place in a solvent such as diethyl ether, tetrahydrofuran or dichloromethane at $-80°$ C. to $+80°$ C. in an inert atmosphere. The product is worked up by quenching with a proton donor. When M is magnesium the organometalic compound is more specifically $R^1(CH_2)_n$Mg halogen or $R^3$ Mg halogen. When M is titanium the organometallic compound is more specifically $R^1(CH_2)_n$Ti(O-alkyl)$_3$ or $R^3$Ti(O-alkyl)$_3$. When M is zirconium the organometallic compound is more specifically $R^1(CH_2)_n$Zr(O-alkyl)$_3$ or $R^3$Zr(O-alkyl)$_3$.

The compound of general formula (I) may also be prepared by reacting a compound of general formula (IV) or (V):

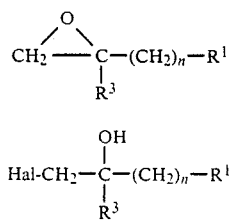

in which $R^1$ and $R^3$ are as defined above and Hal is a halogen atom (preferably a chlorine or bromine atom), with 1,2,4-triazole either in the presence of an acid-binding agent (for example potassium carbonate) or in the form of one of its alkali metal salts in a convenient solvent.

We have found that reaction of the compound of general formula (IV) or (V) with 1,2,4-triazole in the presence of an acid binding compound such as potassium carbonate in a solvent such as dimethylformamide generally gives a mixture in which the 1-substituted triazole predominates and in which the 4-substituted triazole is present as a minor component. The mixture may be used without isolating the position isomers, but, if desired, the isomers may be readily separated, for example by fractional crystalisation or vacuum distillation. We have found conversely that reaction of the compound of general formula (IV) or (V) with an alkali metal salt of 1,2,4-triazole generally produces essentially the 1-substituted triazole.

Thus if it is desired to produce only the 1-substituted triazole the compound of general formula (IV) or (V) may be reacted at 20°–120° C. with the sodium salt of 1,2,4-triazole. The salt can typically be prepared by adding either sodium hydride or sodium methoxide to 1,2,4-triazole in a convenient solvent such as acetonitrile, methanol, ethanol or dimethylformamide. The product can be isolated by pouring the reaction mixture into water and extracting the product with a suitable organic solvent for example diethyl ether, ethyl acetate or dichloromethane.

The ethers (wherein $R^2$ is alkyl) and the esters of the invention are made from the hydroxy compounds by reacting them with the appropriate halide, acid chloride or acid anhydride in the presence of a suitable base.

The compounds of general formula (IV) can be prepared by reacting the appropriate compound of general formula (VI):

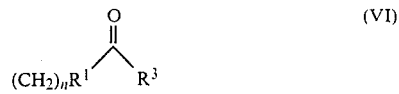

wherein $R^1$ and $R^3$ are as defined above, with dimethylsulphonium methylide (JACS 1962, 84, 3782) or dimethylsulphoxonium methylide (JACS 1965, 87, 1353) using methods set out in the literature.

The ketones of general formula (VI) may be prepared using standard methods set out in the literature.

Compounds of the general formula (IV) and (V) may also be prepared by reacting a compound of general formula (VII a) or (VII b):

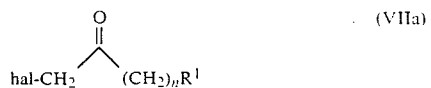

wherein $R^1$, $R^3$ and hal are as defined above, with an organometallic compound of general formula (III b) or (III a).

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals (such as wheat, barley and rice), oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertilizer to be applied. The stunting of woody species is useful in controlling of the growth of trees under power lines etc.

The growth of trees acting as windbreaks, for example in orchards, may be controlled to prevent the need for excessive cutting back of foliage. Control of the growth of conifers may be useful in plantation management. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting.

Growth retardation of grasses can help maintenance of grass swards. Examples of suitable grasses are *Strenotaphrum secundatum* (St. Augustine grass), *Cynosurus cristatus*, *Lolium multiflorum* and *perenne*, *Agrostis tenuis*, *Cynodon dactylon* (Bermuda grass), Dactylisglomerata, Festuca spp. (e.g. *Festuca rubra*) and Poa spp (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses.

The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops.

In fruit orchards, particularly orchards subject to soil erosion, the presence of grassover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturizing ornamental, household, garden and nursery plants (e.g. poinsettias, roses, chrysanthemums, carnations, tulips and daffodils).

As indicated above, the compounds can also be used to stunt woody species. This property can be used to control hedgerows or to shape or reduce the need for pruning, of fruit trees (e.g. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

In addition, the compounds may be useful as abscission agents resulting in the thinning of fruit on the tree and on increase in fruit quality.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, e.g. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (e.g. rice), the number of flowering shoots per unit area may be increased thereby increasing the overall grain yield of such crops. In addition better control and modification of. hierarchical relationships is possible both in vegetative and reproductive stages of monocotyledonous and dicotyledenous plant growth, especially in cereals such as wheat. barley, rice and maize, whereby the number of flowering shoots per unit area may be increased and the size distribution of grains within the ear may be modified in such a way as to increase yield. In the treatment of rice plants, or rice crops the invention compounds can be applied, e.g. as granules or a granular formulation, for example as slow release granules, to nursery boxes, paddy water and other like cultivation loci and media. Paddy rice may be treated by submerged application of granules. In grass swards, especially amenity grass, an increase in tillering could lead to a denser sward which may result in increased resilience in wear; and to increased yields and better quality of forage grass, e.g. improved digestibility and palatability.

The treatment of plants with the compounds can lead to the leaves developing a darker green colour. In dicotyledonous plants such as soybean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g. turnip. swede, mangold. parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (i.e. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed. shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds may have a growth stimulating effect on plants.

It is to be understood that not all the compounds of the present invention will necessarily show all the above mentioned plant growth regulating effects. Compounds which have a broad spectrum of plant growth regulating effects against a wide range of species are clearly beneficial. However, equally useful are compounds which have a high specific activity with respect to a particular species and/or plant growth regulating effect.

The Examples show that the compounds of the present invention are generally very effective as growth retardants on a wide range of species, especially on temperate cereals such as wheat and, barley and also on rice, and apples. The compounds generally show excellent reduction of interligular length. which is one indication of internode length reduction in mature plants and consequent limitation of the susceptibility of cereals to lodging. On woody species such as apples and vines the compounds act as general retardants providing scope for their use as field management aids. The compounds generally have a substantial green up effect associated with the activity and in cereals can influence tillering which may be lead to increased ear number at maturity and hence increases in yield. Certain of the compounds of the present invention show a more specific mode of action. Thus for example compound No 3 is relatively more active on barley and rice than on apples.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.01 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for plant growth regulating purposes but are more conveniently formulated into compositions for such usage. The invention thus provides a plant growth regulating composition comprising a compound of general formula (I) as hereinbefore defined, or a salt, ester or metal complex thereof; and, optionally, a carrier or diluent.

The invention also provides a method of regulating plant growth, which comprises applying to the plant, to seed of a plant or to the locus of a plant or seed, a compound, or a salt, ester or metal complex thereof, as hereinbefore defined, or a composition containing the same.

The compounds, salts metal complexes, and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions of the present invention may also be in the form of dispersible powders, granules or grains comprising a wetting agent to facilitate the dispersion in liquids of the powder or grains which may contain also fillers and suspending agents.

The aqueous dispersions or emulsions may be prepared solving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilizers (e.g. nitrogen-, potassium- or phosphorus-containing fertilizers). Compositions comprising only granules of fertilizer incorporating, for example coated with, the compound are preferred. Such granules suitably contain up to 25% by weight of the compound. The invention therefore also provides a fertilizer composition comprising the compound of general formula (I) or a salt, ester or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also one or more additional compound(s) having biological activity, e.g. compounds having similar or complementary fungicidal or plant growth activity or compounds having, herbicidal or insecticidal activity.

The additional fungicidal compound can be, for example, one which is capable of combating ear diseases of cereals (e.g. wheat) such as Septoria, Gibberella and Helminthosporium spp., seed and soil borne diseases and downy and powdery mildews on grapes and powdery mildew and scab on apple etc. Examples of suitable additional fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetylaluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine fentin acetate, fentin hydroxide, dinocap, folpet, dichlofluanid, ditalimphos, kitazin, cycloheximide, dichlobutrazol, a dithiocarbamate, prochlorez, a copper compound, a mercury compound, 1-(2-cyano-2-methoxyiminoacetyl)-3-ethyl urea, fenaponil, ofurace, propiconazole, etaconazole and fenpropemorph and fenpropidine.

The compounds of general formula (I) can be mixed with soil, peat or other rooting media for the protection of plants against seed-borne, soil-borne or foliar fungal diseases.

Suitable additional insecticides are Pirimor, Croneton, dimethoate, Metasystox, pyrethroid insecticides and formothion.

The other, additional, plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will also be herbicides.

Examples of suitable plant growth regulating compounds, which can display synergy in admixture, or use, with the invention compounds are the gibberellins (e.g. $GA_3$, $GA_4$ and $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine, long chain fatty alcohols and acids, dikegulac, fluoridamid, mefluidide, substituted quaternary ammonium and phosphonium compounds (e.g. chlormequat*, chlorphonium, phosphonl D or mepiquat*), ethephon, carbetamide, methyl-3,6-dichloroanisate, daminozide*, asulam, abscisic acid, isopyrimol. 1-(4-chlorophenyl)-4,6-dimethyl-2-oxo-1,2-dihydropyridine-3-carboxylic acid, hydroxybenzonitriles (e.g. bromoxynil), difenzoquat*, benzoylprop-ethyl 3,6-dichloropicolinic acid, uniconazole, triapenthenol, flurprimidol, paclobutrazol, tetcyclacis tecnazene and amidichlor. Synergy will be most likely to occur with those of the foregoing which are quaternary ammonium compounds and with those marked with an asterisk.

For certain applications, for example in the injection of the compounds of the invention into trees or plants, it is desirable that the compounds have a relatively high solubility in water, for example a solubility in excess of 30 parts per million. The compounds may be used as an aqueous solution or may be formulated for injection, for example as a solution in a lower alcohol.

For certain applications it is also desirable that the compound has a low persistancy in soil to prevent carry-over to adjacent crops or even crops planted subsequently in the same soil. Preferably the compound for use in such applications has a half life in the soil of less than 20 weeks.

The invention is illustrated by the following examples.

EXAMPLE 1

This Example illustrates the preparation of a mixture of Compounds 1 and 2 of Table 1 and their subsequent separation.

Stage 1

Preparation of 2,2-dimethyl-4-cylcopentyl butan-3-one

To a stirred mixture of pivaloyl chloride (11.09 g) and copper (I) iodide (10.0 g) in dry tetrahydrofuran (120 mls) at $-75°$ C. under nitrogen was added dropwise cyclopentyl methylmagnesium bromide [prepared from magnesium turnings (3.313 g) and cyclopentylmethylbromide (15.0 g) in dry tetrahydrofuran (95 mls)]. The cooling bath was removed and the reaction mixture stirred for 16 hours then hydrolysed with cold aqueous ammonium chloride (10%). After filtration and extraction of the filtrates with ether, the combined ethereal extracts were washed with aqueous sodium hydroxide (10%) and brine and were dried over anhydrous magnesium sulphate. Concentration in vacuo gave the crude ketone as a yellow oil which was used without further purification.

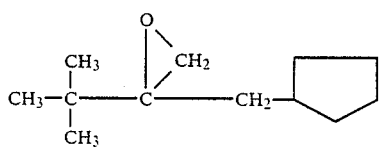

(VIII)

Stage 2

Preparation of the Epoxide of formula VIII

A mixture of the Ketone prepared in Stage 1, trimethylsulphonium iodide (15.3 g), tetrabutylammonium bisulphate (1.0 g) and finely ground potassium hydroxide (8.125 g) in dry dimethylsulphoxide (175 mls) was stirred vigorously at 45° C. for 2½ hours, then 16 hours at 23° C. and finally at 45° C. for 1 hour. Cooled to 20° C. A saturated aqueous sodium bicarbonate solution and brine were added and the mixture was extracted with ether. The combined ethereal extracts were washed with brine, dried over anhydrous magnesium sulphate and concentrated in vacuo to give a yellow oil. This crude epoxide (a racemic mixture) was used without further purification.

Stage 3

A mixture of the epoxide prepared in Stage 2, 1,2,4-triazole (8.19 g) and anhydrous potassium carbonate (17.06 g) in dry dimethyl formamide (100 mls) was stirred vigorously at 100°–110° C. for 5½ hours. After cooling, the mixture was concentrated in vacuo and the residue partitioned between ether and water. The organic layer was separated and the aqueous layer was re-extracted with ether. The combined ethereal layers were washed with brine, dried over anhydrous magnesium sulphate and concentrated in vacuo to leave a very pale yellow viscous oil. Trituration with 30–40 petroleum ether and ether at reduced temperature gave a white solid, which was a mixture of Compound 1 of Table 1 and Compound 2 of Table 1.

Stage 4

The solid from Stage 3 was suspended in ether and stirred at 20° C. for 15 minutes, then cooled to −20° C. The solid was filtered to give Compound 2 of Table 1 as a white powder (0.44 g) melting point 167°–169° C. The filtrates were concentrated in vacuo to leave an oil which gradually crystallized to give Compound 1 of Table I as white crystals (5.67 g) melting point 55.5°–58° C. Compound 1 of Table I is 2,2-dimethyl-3-hydroxy-3-cylopentylmethyl-4-(1,2,4-triazol-1-yl)-butane.

Compound 2 of Table I is 2,2-dimethyl-3-hydroxy-3-cyclopentylmethyl-4-(1,2,4-triazol-4-yl)-butane. The physical characteristics of Compound 1 are as follows:

Compound 1

NMR (CDCl$_3$) 0.96 (9H,s), 0.64–1.20 (2H, complex), 1.24–1.80 (9H, complex), 2.88 (1H,s), 4.22 (1H,d), 4.32 (1H,d), 7.92 (1H,s), 8.17 (1H,s).

IR (nujol) 3600–3050 cm$^{-1}$(m), 3060 cm$^{-1}$)(w).

m/e no M$^+$, 194, 168, 83.

CHN Expected C66.89 H10.03 N 16.72%. Found C66.76 H9.92 N16.31%.

Compound 2

NMR (CDCl$_3$+dmsod$_6$) 0.70–0.96 (2H, complex), 0.99 (9H,s), 1.12–1.81 (9H, complex), 3.58 (1H,s), 4.06 (1H,d), 4.14 (1H,d), 8.38 (2H,s).

IR (nujol) 3600–3100 cm$^{-1}$(m), 3130 cm$^{-1}$ (m-w).

m/e MH$^+$ 252, 194, 169, 83.

EXAMPLE 2

This Example illustrates the preparation of Compound 4 of Table 1.

Stage 1

Preparation of 2,2-dimethyl-3-cyclobutyl propan-3-one

Cuprous iodide (1.0 gm) was added to a solution of cyclobutane carboxylic acid chloride (15.0 gms) in dry ether (40 mls) under an argon atmosphere. The suspension was stirred and cooled to −70° C. A solution of t-butyl magnesium chloride in ether (61.4 mls of 2M solution) was then added dropwise, whilst the temperature was maintained below −70° C. After the addition was complete, stirring was continued at −70° C. for 1 hour and then for several hours whilst the temperature was allowed to reach 20° C. Water was carefully added to the mixture. The ether layer was separated, combined with an extract of the aqueous phase and washed with dilute caustic soda. Drying and evaporation gave 4.9 gms of yellow oily product. Gas chromatography showed 80% of a major component. The product was used without further purification.

Stage 2

Formation of 2-t-butyl-2 cyclobutyl oxirane

A suspension of sodium hydride (from 1.68 gms of petrol-washed 80% oil dispersion) in dimethylsulphoxide (40 mls) was stirred at 60° C. for 1½ hours under a nitrogen atmosphere. The solution was cooled to 20° C., diluted with dry tetrahydrofuran (40 ml) and cooled to −5° C. A slurry of trimethylsulphonium iodide (11.42 gms) in dimethyl sulphoxide (30 mls) was added followed, after 10 minutes stirring, by a solution of the product of Stage 1 (4.9 g) in Tetrahydrofuran (30 mls). The mixture was stirred for 2 hours at −5° C., stood overnight at 20° C., and poured into water and extracted with petrol (30°–40° C.). The extracts were washed with brine, dried and evaporated to give 4.67 gms of yellow product. Gas chromatography showed 75% of a major component. The product was used without further purification.

Stage 3

Preparation of Compound 4 of Table 1

1,2,4-Triazole (2.97 gms) was added to dimethylformamide (40 mls) containing sodium hydride (from 1.29 gms of petrol-washed 80% oil dispersion). After 1½ hours stirring at 20° C. a solution of the product of Stage 2 (4.36 g) in N, N'-dimethyl-propylene urea (10 mls) was added. The mixture was then heated at 80° C. for a total of 12 hours, poured into water and extracted with ether. The extracts were washed with water, dried and concentrated to a white solid which was recrystallized once from ether and once from ethyl acetate to give 1.32 gms of Compound No 6 of Table I. 2,2-dimethyl-3-hydroxy-3-cyclobutyl-4-(1,2,4-triazol-1-yl)-butane melting point 94°–99.5° C.

The physical characteristics are listed below:

NMR (CDCl$_3$) 0.92 (9H,s), 1.12–1.32 (1H, complex), 1.44–2.18 (5H, complex), 2.60–2.80 (1H, complex), 3.34 (1H,s), 4.08–4.32 (2H, quartet), 7.92 (1H,s), 8.12 (1H,s).

IR (nujol) 3060–3140 cm$^{-1}$(m), 3140–3620 cm$^{-1}$(m).

EXAMPLE 3

The general procedure of Example 2 was followed except that cyclopropane carboxylic acid chloride was used as starting material and that in place of cuprous iodide and t-butyl magnesium chloride in stage 1, then was used a mixed organic metallic reagent (tBuO) (tBu)Cu Li prepared from tBuO Li, cuprous iodide and tBu Li, where tBu is the tertiary butyl group (Posner, Whitten and Sterling JACS 95 3 7788, 1973). The product was compound 3 of Table 1, 2-2-dimethyl-3-hydroxy-3-cyclopropyl-4-(1,2,4-triazol-1-yl)butane melting point 80.5°–82.5° C. The product was characterized as follows:

IR (nujol) 3140–3620 cm$^{-1}$(m), 3060–3140 cm$^{-1}$(m).

NMR (CDCl$_3$) (−0.1)–(−0.24) (1H, complex), (−0.66)–(0.78) (1H, complex), 0.24–0.38 (2H, complex), 0.68–0.82 (1H, complex), 1.09 (9H,s), 2.0 (1H,s), 4.28–4.46 (2H, quartet), 7.96 (1H,s), 8.12 (1H,s)

EXAMPLE 4

The general procedure of Example 2 was followed using cyclohexyl carboxylic acid chloride as starting material to give Compound No 5 of Table I, 2,2-dimethyl-3-hydroxy-3-cyclohexyl-4-(1,2,4-triazol-1-yl)-butane melting point 100.5°–101.5° C. The product was characterized as follows:

IR 3160–3540 cm$^{-1}$ (s).

NMR (CDCl$_3$) 1.03 (9H,s), 0.28–2.08 (11H, complex), 3.58 (1H,s), 4.16–4.6 (2H, quartet), 8.00 (1H,s), 8.24 (1H,s).

EXAMPLE 5

The general procedure of Example 2 was followed using cyclobutylacetic acid chloride as starting material to give Compound No 6 of Table 1, 2-2-dimethyl-3-hydroxy-3-cyclobutylmethyl-4-(1,2,4-triazol-1-yl)-butane melting point 73°–75° C. The physical characteristics were as follows:

NMR (CDCl$_3$) 0.96 (9H,s), 1.36–2.0 (9H, complex, 2.68 (1H,s), 4.12–4.32 (2H, quartet), 7.96 (1H,s), 8.16 (1H,s).

EXAMPLE 6

This Example illustrates the preparation of Compound No 7 of Table 1.

Stage I

To a stirred mixture of pivaloyl chloride (7.2 g) and copper (I) iodide (0.76 g) in dry ether (100 ml) at −60° C. under nitrogen was added dropwise cyclohexylmethyl magnesium bromide (prepared from magnesium turnings (1.80 g) and cyclohexylmethyl bromide (8.85 g) in dry ether (100 mls). The cooling bath was removed and the reaction mixture stirred for 16 hours then poured cautiously into ice-cold dilute hydrochloric acid and extracted with ether. The combined ethereal extracts were washed with saturated aqueous sodium hydrogen carbonate, brine, dried (anhydrous magnesium sulphate) and the ether removed in vacuo to give the crude ketone as a brown oil which was used without further purification.

Stage II

A suspension of sodium hydride (50% (3.46 g) prewashed with petroleum ether (40°–60° C.) in dry dimethylsulphoxide (100 mls) was heated at 60° C. for 2 hours. The mixture was cooled to room temperature, dry tetrahydrofuran (80 mls) added and then further cooled at 0° C. Trimethylsulphonium iodide (14.7 g) dissolved in dry dimethyl sulphonide (80 mls) was added dropwise keeping the temperature of the mixture at below 3° C. After complete addition of the trimethylsulphosium iodide solution the mixture was stirred for one more minute and then a solution of the ketone, prepared as described in Stage I, in dry tetrahydrofuran (20 mls) was added rapidly. After stirring at 0° C. for 1 hour the cooling bath was removed and the reaction mixture was stirred for 16 hours. The reaction mixture was poured into water and extracted with ether. The combined ethereal extracts were washed with brine, dried over anhydrous magnesium sulphate and the ether removed in vacuo to give the epoxide as a pale yellow oil which was used without further purification.

Stage 3

Preparation of Compound No 7 of Table 1

To a suspension of sodium hydride (50%) (3.26 g) in dry dimethylformamide (100 mls) was added portionwise, 1,2,4-triazole (4.7 g). The reaction mixture was stirred at room temperature for 20 minutes. Then the epoxide prepared in Stage 2 was added dropwise. The resultant mixture was heated at 80° C. for 6 hours, cooled and then poured into water and extracted with ether. The combined ethereal extracts were washed with brine, dried over anhydrous magnesium sulphate and evaporated. The residue was chromatographed on silica using gradient elution (ethyl acetate (0–100%) in petrol) to give Compound No 9 of Table I (0.89 g) melting point 81.5°–83° C.

2-2-Dimethyl-3-hydroxy-3-cyclohexylmethyl-4-(1,2,4-triazole-1-yl)-butane.

NMR (CDCl$_3$) 0.97 (9H,s), 0.7–1.8 (13H, complex), 2.96 (1H,s), 4.24 (2H, AB quartet), 7.97 (1H,s), 8.15 (H,s).

IR (nujol) 3000–3600, 3160 cm$^{-1}$.

m/e no M$^+$, 208, 183, 168, 83, 70.

EXAMPLE 7 to 15

Compound Nos. 8 to 16 of Table I were prepared using the general method of Example 2 and the melting points are listed in that Table. Where the product was an oil or a mixture of diastereoisomers, the product is further characterized by nuclear magnetic resonance data which is presented in Table II below in which all values are given in terms of $\delta_H$.

The manner in which the compounds of the present invention may be formulated into compositions suitable for application is shown generally in the following indicative illustrations numbered as Examples 16 to 25.

TABLE II

| COMPOUND NO. | NMR (90 MHz; CDCl$_3$) |
|---|---|
| 9 | 8.16, (1H, s); 7.96 (1H, s); 4.35, 4.30, 4.25, 4.20 (4 singlets, collectively 2H); 2.78, 2.76, 2.72, 2.68 (4 singlets, collectively 1H); 1.4–1.95 (22H, complex). |
| 10 | 8.16–8.20 (1H, superimposed singlets); 7.92–7.96 (1H, superimposed singlets); |

TABLE II-continued

| COMPOUND NO. | NMR (90 MHz; CDCl₃) |
|---|---|
|  | 4.12–4.36 (2H, complex), 3.0, 2.96, 2.90, 2.76 (4 singlets, collectively 1H); 1.6–2.0 (22H, complex). |
| 11 | 8.05 (1H, s); 7.95 (1H, s); 4.24–4.36 (2H, superimposed singlets); 2.96 (1H; s); 0.3–1.2 (14H, complex); −0.2 to −0.615 (2H, complex). |
| 12 | 8.16–8.2 (1H, superimposed singlets); 7.96–8.0 (1H, superimposed singlets); 5.56–5.68 (1H, complex); 5.28–5.4 (1H, complex); 4.2–4.4 (2H, complex); 3.10, 2.98 (2 singlets, collectively 1H); 1.2–2.3 (7H, complex); 1.0 (9H, superimposed singlets). |
| 14 | 8.17 (1H, s); 7.95 (1H. s); 2.80, 2.76, 2.74, 2.71 (4 singlets, collectively 1H); 4.36, 4.28, 4.24, 4.20 (4 singlets, collectively 1H); 0.8–1.8 (15H, complex); 0.98 (9H, s). |
| 15 | 8.17 (1H, superimposed singlets); 7.98 (1H, superimposed singlets); 4.15–4.35 (2H, complex); 2.96 (2, superimposed singlets), 2.91, 2.8 (4 singlets, collectively 1H); 0.48–2.0 (24H, complex). |
| 16 | 8.16 (1H, superimposed singlets); 7.92 (1H, superimposed singlets); 4.1–4.35 (2H, complex); 2.92, 2.88, 2.86, 2.72 (4 singlets, collectively 1H); 0.6–2.1 (2H, complex). |

EXAMPLE 16

An emulsified concentrate is made up by mixing the following ingredients, and stirring the mixture until all the constituents were dissolved.

| Compound of Table I | 10% |
|---|---|
| Calcium dodecylbenzensulphate | 5% |
| "SYNPERONIC" NP13 | 5% |
| "Aromasol" H | 80% |

EXAMPLE 17

A composition in the form of grains readily dispersible in a liquid, e.g. water, is prepared by grinding together the first three ingredients in the presence of added water and then mixing in the sodium acetate. The resultant mixture is dried and passed through a British Standard mesh sieve, size 44–100, to obtain the desired size of grains.

| Compound of Table I | 50% |
|---|---|
| "Dispersol" T | 25% |
| "SYNPERONIC" NP5 | 1.5% |
| Sodium acetate | 23.5% |

EXAMPLE 18

The following ingredients are ground together to produce a powder formulation readily dispersible in liquids.

| Compound of Table I | 45% |
|---|---|
| "Dispersol" T | 5% |
| "SYNPERONIC" NX | 0.5% |
| "Cellofas" B600 | 2% |
| China clay GTY powder | 47.5% |

EXAMPLE 19

The active ingredient is dissolved in acetone and the resultant liquid is sprayed on to the granules of attapulgite clay. The solvent is then allowed to evaporate to produce a granular composition.

| Compound of Table I | 5% |
|---|---|
| Attapulgite granules | 95% |

EXAMPLE 20

A composition suitable for use as a seed dressing is prepared by mixing the three ingredients.

| Compound of Table I | 50% |
|---|---|
| Mineral oil | 2% |
| China clay | 48% |

EXAMPLE 21

A dusting powder is prepared by mixing the active ingredient with talc.

| Compound of Table I | 5% |
|---|---|
| Talc | 95% |

EXAMPLE 22

A flowable formulation is prepared by bead-milling the constituents set out below and then forming an aqueous suspension of the ground mixture with water.

| Compound of Table I | 40% |
|---|---|
| "Dispersol" T | 4% |
| "SYNPERONIC" NP5 | 1% |
| Water | 55% |

EXAMPLE 23

A dispersible powder formulation is made by mixing together the ingredients set out below and then grinding the mixture until all were thoroughly mixed.

| Compound of Table I | 25% |
|---|---|
| "Aerosol" OT/B | 2% |
| "Dispersol" A.C. | 5% |
| China clay | 28% |
| Silica | 40% |

EXAMPLE 24

This Example illustrates the preparation of a dispersible powder formulation. The ingredients are mixed and the mixture then ground in a comminution mill.

| Compound of Table I | 25% |
|---|---|
| "PERMINAL" BX | 1% |
| "Dispersol" T | 5% |
| Polyvinylpyrrolidone | 10% |
| Silica | 25% |

-continued

| | |
|---|---|
| China clay | 34% |

EXAMPLE 25

The ingredients set out below are formulated into dispersible powder by mixing then grinding the ingredients.

| | |
|---|---|
| Compound of Table I | 25% |
| "Aerosol" OT/B | 2% |
| "Dispersol" A | 5% |
| China clay | 68% |

In Examples 16 to 25 the proportions of the ingredients given are by weight.

There now follows an explanation of the compositions or substances represented by the various Trade Marks and Trade Names mentioned above.

"SYNPERONIC" NP13: a condensate of nonyl phenol (1 mole) with ethylene oxide (13 moles).

"AROMASOL" H: a solvent mixture of alkylbenzenes.

"DISPERSOL" T AND AC: a mixture of sodium sulphate and a condensate of formaldehyde with sodium naphthalene sulphonate.

"SYNPERONIC" NP5 a condensate of nonyl phenol (1 mole) with naphthalene oxide (5.5 moles).

CELLOFAS B600: a sodium carboxymethyl cellulose thickener.

EXAMPLE 26

Whole Plant Screen

Compounds of the present invention were tested on a whole plant screen. The compounds were tested for plant growth regulator activity against five species for various growth effects relevant to plant growth regulation.

Methodology

The plant species used in this screen are presented in Table III with the leaf stage at which they were sprayed. Each chemical was applied at 4000 ppm (4 kg/ha in a 1000 l/ha field volume) using a tracksprayer and a SS8004E (Teejet) nozzle.

After spray the plants were grown in a glasshouse with 25° C. day/22° C. night temperatures. The exception to this were the temperate cereals, wheat and barley which are grown in 13°–16° C. day/11°–13° C. night temperatures. Supplementary lighting was supplied when necessary to provide an average photoperiod of 16 hours (14 hours minimum).

After 2-6 weeks in the glasshouse, depending on species and time of year, the plants were visually assessed for morphological characteristics. Formulation blanks were used as controls to assess the plants against. The results are presented in Table IV.

TABLE III

PLANT MATERIAL USED FOR WHOLE PLANT SCREEN

| Species | Code | Variety | Growth Stage at Treatment | No. Plants per 3" Pot | Compost Type |
|---|---|---|---|---|---|
| Barley | BR | Atem | 1–1.5 leaves | 4 | JIP* |
| Wheat | WW | Timmo | 1–1.5 leaves | 4 | JIP |
| Maize | MZ | Earliking | 2¼–2½ leaves | 1 | PEAT |
| Apple | AP | Red Delicious | 4–5 leaves | 1 | JIP |
| Rice | RC | Ishikari | 2–2½ leaves | 4 | JIP |

JIP* = John Innes Potting Compost.

TABLE IV

| SPECIES | COMPOUND NO | R | G | A | T | I |
|---|---|---|---|---|---|---|
| BR | 1 | 2 | 1 | | | 3 |
| BR | 2 | 1 | | | | 1 |
| BR | 3 | 3 | 1 | | 1 | 3 |
| BR | 4 | | | | | |
| BR | 5 | 1 | | | | 2 |
| BR | 8 | 1 | | | | |
| BR | 10 | 2 | | | | 2 |
| BR | 11 | 2 | | | | 2 |
| BR | 12 | 1 | | | 2 | 1 |
| BR | 13 | 1 | | | | 1 |
| WW | 1 | 2 | 1 | | | 3 |
| WW | 2 | 1 | 1 | | | 3 |
| WW | 3 | 2 | 2 | | | 3 |
| WW | 4 | | | | | |
| WW | 5 | 2 | 1 | | | 3 |
| WW | 6 | 3 | 2 | | 1 | 3 |
| WW | 8 | 1 | | | 1 | 2 |
| WW | 10 | 3 | | | 1 | 3 |
| WW | 11 | 2 | 1 | | 1 | 3 |
| WW | 12 | 2 | | | 2 | 3 |
| WW | 13 | 2 | 2 | | 2 | 3 |
| RC | 1 | 2 | 1 | | 3 | 3 |
| RC | 2 | 1 | | | 1 | 1 |
| RC | 3 | 2 | 1 | | 1 | 3 |
| RC | 4 | | | | | |
| RC | 5 | 1 | 1 | | 2 | 1 |
| RC | 8 | | | | | |
| RC | 10 | 2 | 1 | | | 3 |
| RC | 11 | 1 | | | | 2 |
| RC | 12 | 2 | | | 1 | 2 |
| RC | 13 | 1 | | | | 3 |
| MZ | 1 | 1 | | 1 | | 1 |
| MZ | 2 | | | | | |
| MZ | 3 | 1 | | | | 1 |
| MZ | 4 | | | | | |
| MZ | 5 | | | | | |
| MZ | 8 | | | | | |
| MZ | 10 | | | | | |
| MZ | 11 | | | | | |
| MZ | 12 | 2 | | | | 2 |
| MZ | 13 | 1 | | | | |
| AP | 1 | 3 | 1 | | 2 | 3 |
| AP | 2 | | | | | |
| AP | 3 | | | | | |
| AP | 4 | | | | | |
| AP | 5 | 3 | | 3 | 2 | 1 |
| AP | 8 | 3 | 1 | 3 | 3 | 3 |
| AP | 10 | 3 | 1 | 3 | 2 | 3 |
| AP | 11 | 1 | | | | 1 |
| AP | 12 | 1 | | | 1 | 1 |

Key:
R = Retardation
G = Greening effect
A = Apical damage
T = Tillering or tuber sprouting
I = Interligular or internodal length reduction
All effects are scored visually on a 1-3 basis where
1 = 10–30%
2 = 31–60%
3 = 61–100%
Blank means less than 10% effect

EXAMPLE 27

Whole Plant Screen

Compound number 7 of Table 1 was tested on an alternate whole plant screen. The compounds were tested for plant growth regulator activity against up to thirteen plant species for various growth effects relevant to plant growth regulation. The methodology was as in Example 17 and the plant species used are present in Table V. With the leaf stage at which they were sprayed.

The results are presented in Table VI.

indicates that the Compound was not tested. A blank indicates that no retardant effect was observed.

TABLE VII

PLANT MATERIAL FOR INTERMEDIATE RETARDANT TEST

TABLE V

PLANT MATERIAL USED FOR ALTERNATIVE WHOLE PLANT SCREEN

| Species | Code | Variety | Growth Stage at Treatment | No. Plants per 3" Pot | Compost Type |
|---|---|---|---|---|---|
| Barley | BR | Atem | 1–1.5 leaves | 4 | JIP* or PEAT |
| Wheat | WW | Timmo | 1–1.5 leaves | 4 | JIP of PEAT |
| Maize | MZ | Earliking | 2¼–2½ leaves | 1 | PEAT |
| Vines | VN | Ohanez + Unspecified | 4 leaves | 1 | PEAT |
| Soya | SY | Amsoy | 1st trifoliate | 1 | JIP |
| Tomato | TO | Ailsa Craig | 1.5–2 leaves | 1 | PEAT |
| Lettuce | LT | Verpia | 3–4 leaves | 1 | PEAT |
| Sugar Beet | SB | Amono | 2 leaves | 1 | PEAT |
| *Agrostis tenius* | AT | | cut to 2 cm | Grown in rows | |
| *Cynosurus cristatus* | OC | | 48 hours before | in plastic | PEAT |
| *Dacrylis glomerata* | DA | | treatment | punnets | |
| Radish | RA | Istar | seeds | 4 | PEAT |

JIP* = John Innes Potting Compost.

TABLE VI

| COMPOUND NO | WW | BR | MZ | AT | CC | DA | SY | SB | TO | VN | RA | LT |
|---|---|---|---|---|---|---|---|---|---|---|---|---|
| 7 | 2 | 2 | 1 | 3 | 3 | 1 | 3GA | 2G | 3GAT | 3GAT | 1G | 1G |

Key:
Retardation 1–3 where
1 = 10–30%
2 = 21–60%
3 = 61–100%
Greening effect = G
Apical damage = A
Tillering or side shooting = T
Blank means less than 10% effect
— indicates that the compound was not tested against this species

EXAMPLE 28

Intermediate Retardant Test

Methodology

Three species are involved in this test RICE, SPRING BARLEY and APPLES. The variety and growth stages at spray are outlined in Table VII. Compounds were applied at 1000 ppm and 4000 ppm respectively (1 kg and 4kg ha$^{-1}$ at a field volume of 1000 ha$^{-1}$) as an overall spray. This gives a foliar and root component in the test, i.e. this test will detect the activity of both root and foliar acting compounds. The rice was grown in 4" 'paddy' pots, i.e. the roots and bottom of the stems are immersed in water under conditions corresponding to those in paddy fields. Spring barley and apples were grown in 4" pots. The plants were assessed for height to top-most ligule at approximately 28 days after treatment for spring barley and rice and for height to apex between 14 and 28 days after treatment for apples, (depending on time of year and growth stage). The results are presented in Tables VIII to IX. In each case the result for the 1000 ppm and 4000 ppm test for each compound is compared to the height of the formulation blank in that test and presented as a percentage reduction in height compared to the formulation blank.

The Compounds tested are indicated by their Compound No in Table 1, apart from "Compound No A" which was a mixture of Compound 1 and Compound 2 of the type produced in Stage 3 of Example 1. A dash (-)

| Species | Variety | Growth Stage at Treatment | No. Plants per 4" Pot | Compost Type |
|---|---|---|---|---|
| Spring Barley | Atem | 3 leaves | 4 | JIP 1 |
| Rice | Ishikari | 3–4 leaves | 2 | SM2:JIP 1 |
| Apples | Red Delicious | 5–10 cm high | 1 | SM2:JIP 1 |

JIP 1 = John Innes Potting Compost.
SM2 = a mixture of loam and grit.

TABLE VIII

Percentage Reduction in Height of Rice
(Compound to formulation blank)

| | Rate | |
|---|---|---|
| COMPOUND NO | 1000 ppm | 4000 ppm |
| 1 | 48.1 | 65.4 |
| 2 | 10.6 | 32.4 |
| 3 | 3.5 | 21.4 |
| 4 | 2.2 | 4.9 |
| 5 | 10.9 | 37.7 |
| A | 45.3 | — |
| 7 | — | — |
| 10 | 43 | 52 |

TABLE IX

Percentage Reduction in Height of Spring Barley
(Compared to formulation blank)

| | Rate | |
|---|---|---|
| COMPOUND NO | 1000 ppm | 4000 ppm |
| 1 | 35.8 | 71.2 |
| 2 | | 25.3 |
| 3 | 4.1 | 49.1 |
| 4 | 2.2 | 5.6 |
| 5 | 10.7 | 51.2 |

TABLE IX-continued

Percentage Reduction in Height of Spring Barley
(Compared to formulation blank)

| COMPOUND NO | Rate | |
|---|---|---|
| | 1000 ppm | 4000 ppm |
| A | 15.7 | — |
| 7 | 11.7 | 47.0 |
| 10 | 7 | 51 |

TABLE X

Percentage Reduction in Height of Apples
(Compared to formulation blank)

| COMPOUND NO | Rate | |
|---|---|---|
| | 1000 ppm | 4000 ppm |
| 1 | 53.1 | 67.0 |
| 2 | 5.2 | 15.6 |
| 3 | | 1.9 |
| 4 | 12.7 | 31.3 |
| 5 | 29.3 | 47.8 |
| A | 10.4 | — |
| 7 | | 57.5 |
| 10 | 37 | 77 |

We claim:

1. A trizole derivative having the formula (I):

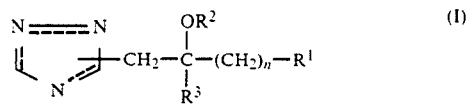

and stereoisomers thereof, wherein $R^1$ is a cycloalkyl or cycloalkenyl group containing from 3 to 8 carbon atoms in the cycloalkyl or cycloalkenyl ring, the cycloalkyl or cycloalkenyl ring being optionally substituted by from one to two substituents selected from the group consisting of alkyl of 1-4 carbons and halogen; n is 0 or 1; $R^2$ is hydrogen; and $R^3$ is tertiary butyl optionally substituted by one or two halogen atoms.

2. A triazole derivative according to claims 1 wherein $R^1$ is the group cyclopropyl, cyclobutyl, cyclopentyl, cyclohexyl or cyclopentenyl, each of which may be optionally substituted by one to two methyl or ethyl groups.

3. A triazole derivative according to any of the preceding claims wherein $R^3$ is tertiary butyl.

4. A triazole derivative according to claim 1 which is a triazol-1-yl derivative.

5. A plant growth regulating composition comprising an effective amount of a triazole derivative according to claim 1 and an inert carrier or diluent therefor.

6. A method of regulating plant growth which comprises applying to the plant, or to the locus of the plant an effective amount of a triazole derivative according to claim 1.

* * * * *